United States Patent
Tsubuki et al.

(10) Patent No.: US 9,315,453 B2
(45) Date of Patent: Apr. 19, 2016

(54) 4-(3-BENZYLOXYPHENYLTHIO)-2-CHLORO-1-(3-NITROPROPYL)BENZENE CRYSTAL

(71) Applicant: KYORIN PHARMACEUTICAL CO., LTD., Tokyo (JP)

(72) Inventors: Takeshi Tsubuki, Tochigi (JP); Hiroya Sato, Tochigi (JP)

(73) Assignee: KYORIN PHARMACEUTICAL CO., LTD., Tokyo (JP)

( * ) Notice: Subject to any disclaimer, the term of this patent is extended or adjusted under 35 U.S.C. 154(b) by 0 days.

(21) Appl. No.: 14/385,854

(22) PCT Filed: Apr. 17, 2013

(86) PCT No.: PCT/JP2013/002585
§ 371 (c)(1),
(2) Date: Sep. 17, 2014

(87) PCT Pub. No.: WO2013/157255
PCT Pub. Date: Oct. 24, 2013

(65) Prior Publication Data
US 2015/0073178 A1 Mar. 12, 2015

(30) Foreign Application Priority Data
Apr. 18, 2012 (JP) .................................. 2012-094758

(51) Int. Cl.
*C07C 323/20* (2006.01)
*C07C 319/28* (2006.01)

(52) U.S. Cl.
CPC ............. *C07C 323/20* (2013.01); *C07C 319/28* (2013.01); *C07B 2200/13* (2013.01)

(58) Field of Classification Search
CPC ............................ C07C 323/20; C07C 319/28
See application file for complete search history.

(56) References Cited

FOREIGN PATENT DOCUMENTS

| WO | 03/029205 | 4/2003 |
|---|---|---|
| WO | 2006/041019 | 4/2006 |
| WO | 2009/119395 | 10/2009 |

OTHER PUBLICATIONS

Morissette et al. Advanced Drug Delivery Reviews 2004, 56, 275-300.*
International Search Report issued May 21, 2013 in International (PCT) Application No. PCT/JP2013/002585.
International Preliminary Report on Patentability issued Nov. 18, 2014 in International (PCT) Application No. PCT/JP2013/002585.

* cited by examiner

*Primary Examiner* — Clinton Brooks
(74) *Attorney, Agent, or Firm* — Wenderoth, Lind & Ponack, L.L.P.

(57) ABSTRACT

[Problem] For example, 4-(3-benzyloxyphenylthio)-2-chloro-1-(3-nitropropyl)benzene (compound 1) is used as an intermediate for producing a 2-amino-2-[2-[4-(3-benzyloxyphenylthio)-2-chlorophenyl]ethyl]-1,3-propanediol hydrochloride which has excellent immunosuppressive activity. This compound 1 is traditionally obtained only as an oil and thus handling and refining were difficult.
[Solution] A crystal of the compound 1 is obtained. A method of crystallizing the same is also established. Furthermore, a simple refining method is also found which comprises stirring in suspension the crystal in a solvent. Since the compound 1 can be obtained as a crystal, it is easier to handle and long term storage is possible.

8 Claims, 1 Drawing Sheet

4-(3-BENZYLOXYPHENYLTHIO)-2-CHLORO-1-(3-NITROPROPYL)BENZENE CRYSTAL

TECHNICAL FIELD

The present invention relates to a crystal of 4-(3-benzyloxyphenylthio)-2-chloro-1-(3-nitropropyl)benzene, for example, used as an intermediate for producing 2-amino-2-[2-[4-(3-benzyloxyphenylthio)-2-chlorophenyl]ethyl]-1,3-propanediol hydrochloride and to a method of crystallizing 4-(3-benzyloxyphenylthio)-2-chloro-1-(3-nitropropyl)benzene.

BACKGROUND ART

2-Amino-2-[2-[4-(3-benzyloxyphenylthio)-2-chlorophenyl]ethyl]-1,3-propanediol hydrochloride is a compound having a substituted diaryl sulfide structure that has excellent immunosuppressive action. This compound has been reported to have effectiveness against autoimmune diseases such as rheumatoid arthritis (Patent Literature 1). One method of producing this compound has been reported in Patent Literature 2.

CITATION LIST

Patent Literature

Patent Literature 1: WO03/029205 pamphlet
Patent Literature 2: WO06/041019

SUMMARY OF INVENTION

Technical Problem

In Examples in Patent Literature 2, 4-(3-benzyloxyphenylthio)-2-chloro-1-(3-nitropropyl)benzene was obtained as an oily product.

From the viewpoint of ease of storage and transportation, stability during long-term storage, etc., it is preferable that even an intermediate for producing the compound be obtained as a crystal.

It is an object of the present invention to provide a 4-(3-benzyloxyphenylthio)-2-chloro-1-(3-nitropropyl)benzene crystal.

Solution to Problem

The present inventors have conducted extensive studies to achieve the above object and unexpectedly found a crystal of 4-(3-benzyloxyphenylthio)-2-chloro-1-(3-nitropropyl)benzene represented by the following formula (1).

[Chemical Formula 1]

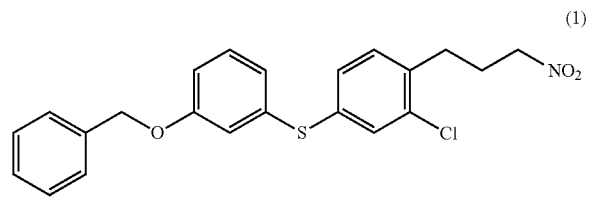

(1)

The present inventors have also conducted extensive studies on a method of crystallizing the compound and found that crystallization is possible by mixing 4-(3-benzyloxyphenylthio)-2-chloro-1-(3-nitropropyl)benzene with an alcohol.

The present inventors have also conducted extensive studies on the crystallization method and found that the crystallization can be more efficiently performed by using, as a seed crystal, a small amount of a crystal that can be obtained by placing a mixture of the compound 1 and an alcohol at a very low temperature.

The present inventors have also found that the crystal of 4-(3-benzyloxyphenylthio)-2-chloro-1-(3-nitropropyl)benzene can be easily purified by suspending and stirring the crystal in a lipophilic solvent in which the crystal exhibits poor solubility.

The present invention includes the following aspects.

[1] A crystal of 4-(3-benzyloxyphenylthio)-2-chloro-1-(3-nitropropyl)benzene, wherein, in powder X-ray diffraction using CuKα radiation with 2θ representing a diffraction angle, a powder X-ray diffraction image including the following 2θ peaks is observed:
2θ: 9.7, 12.9, 16.4, 16.8, 17.6, 19.5, 21.7, 22.6, 22.9, 23.3, 24.5, 24.8, 26.0, 26.4, 27.2.

[2] A crystal of 4-(3-benzyloxyphenylthio)-2-chloro-1-(3-nitropropyl)benzene, wherein a powder X-ray diffraction image substantially the same as an image in FIG. 1 is obtained by powder X-ray diffraction using CuKα radiation with 2θ representing a diffraction angle.

[3] The crystal of 4-(3-benzyloxyphenylthio)-2-chloro-1-(3-nitropropyl)benzene according to [1] or [2], wherein a melting point of the crystal measured by a hot plate method is 46° C. to 49° C.

[4] The crystal of 4-(3-benzyloxyphenylthio)-2-chloro-1-(3-nitropropyl)benzene according to any one of [1] to [3], wherein, in thermogravimetric/differential thermal analysis (TG/DTA) of the crystal, no reduction in weight is observed until 49° C., and a single endothermic peak is observed at around 50° C.

[5] A production method of the crystal according to any one of [1] to [4], the method including the step of mixing 4-(3-benzyloxyphenylthio)-2-chloro-1-(3-nitropropyl)benzene with an alcohol.

[6] The production method according to [5], wherein the 4-(3-benzyloxyphenylthio)-2-chloro-1-(3-nitropropyl)benzene is dissolved in a soluble solvent that can dissolve the compound to obtain a solution, and the obtained solution of the 4-(3-benzyloxyphenylthio)-2-chloro-1-(3-nitropropyl)benzene is mixed with the alcohol to form a mixture of the 4-(3-benzyloxyphenylthio)-2-chloro-1-(3-nitropropyl)benzene and the alcohol.

[7] The production method according to [6], wherein the soluble solvent is ethyl acetate.

[8] The production method according to any one of [5] to [7], wherein the alcohol is methanol, ethanol, 1-propanol, 2-propanol, or a mixture thereof.

[9] The production method according to any one of [5] to [8], the method including the step of adding water to the mixture containing the 4-(3-benzyloxyphenylthio)-2-chloro-1-(3-nitropropyl)benzene and the alcohol.

[10] The production method according to any one of [5] to [9], wherein the crystal is precipitated while a temperature of the mixture containing the 4-(3-benzyloxyphenylthio)-2-chloro-1-(3-nitropropyl)benzene and the alcohol is controlled within a range of −80° C. to +10° C.

[11] A purification method of 4-(3-benzyloxyphenylthio)-2-chloro-1-(3-nitropropyl)benzene, the method including the step of suspending and stirring the crystal according to any one of [1] to [4] in a lipophilic solvent in which the crystal exhibits poor solubility.

[12] The purification method according to [11], wherein the lipophilic solvent is a solvent mixture of hexane and diisopropyl ether.

Advantageous Effects of Invention

According to the present invention, a crystal of 4-(3-benzyloxyphenylthio)-2-chloro-1-(3-nitropropyl)benzene can be provided.

DESCRIPTION OF EMBODIMENTS

Figure 1:
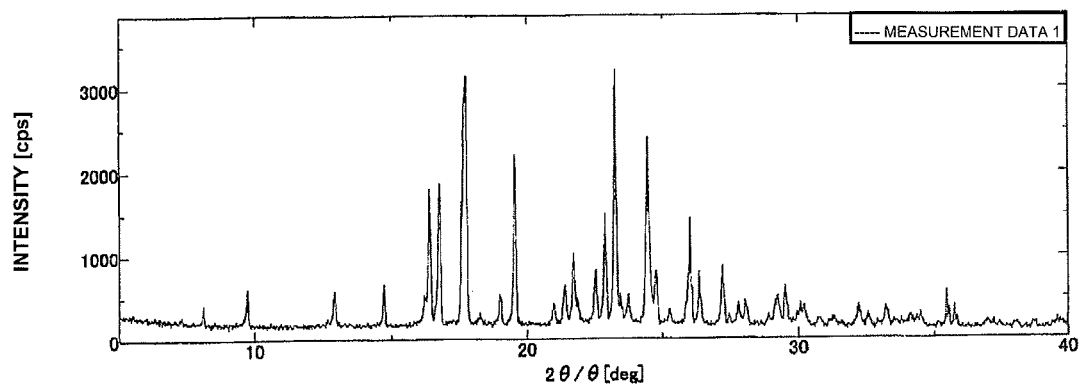
FIG. 1 is a diagram showing the results of powder X-ray diffraction measurement on a crystal of 4-(3-benzyloxyphenylthio)-2-chloro-1-(3-nitropropyl)benzene in an Example.

"4-(3-Benzyloxyphenylthio)-2-chloro-1-(3-nitropropyl) benzene" according to an embodiment (hereinafter referred to as compound 1) can be, for example, used as an intermediate for producing 2-amino-2-[2-[4-(3-benzyloxyphenylthio)-2-chlorophenyl]ethyl]-1,3-propanediol hydrochloride. The compound 1 can be produced as an oily product using, for example, the method described in Patent Literature 2.

Method of Crystallizing Compound 1

Crystals of the compound 1 can be precipitated by mixing the oily compound 1 and an alcohol. Examples of the alcohol may include methanol, ethanol, 1-propanol, 2-propanol, and mixtures thereof, and preferred examples of the alcohol include methanol and ethanol. The use of methanol or ethanol as the alcohol used for mixing allows the crystals to be easily precipitated.

From the viewpoint of facilitating the crystallization and crystallization operation, it is preferable to mix the compound 1 and the alcohol by dissolving the compound 1 in a soluble solvent and then mixing the obtained solution of the compound 1 with the alcohol. The mixing may be performed by adding the solution obtained by dissolving the compound 1 in the soluble solvent to the alcohol or adding the alcohol to the solution obtained by dissolving the compound 1 in the soluble solvent.

To improve a recovery, it is preferable to add water to the mixture of the compound 1 and the alcohol. Specifically, for example, after the mixture of the alcohol and the solution of the compound 1 in the soluble solvent is obtained, water may be added to the obtained mixture.

In the present specification, the "soluble solvent" means a solvent that can dissolve the compound 1 at normal temperature. In the present description, the normal temperature means 15 to 25° C. defined by the Japanese Pharmacopoeia.

Examples of the soluble solvent may include: nitrile solvents such as acetonitrile; ketone solvents such as acetone and 2-butanone; ester solvents such as ethyl acetate and butyl acetate; ether solvents such as tetrahydrofuran; hydrocarbon solvents such as toluene; and mixtures thereof. Mixtures of diisopropyl ether and alcohols can also be used as the soluble solvent. Examples of the alcohol contained in the soluble solvent may include methanol, ethanol, 1-propanol, 2-propanol, and mixtures thereof.

From the viewpoint of facilitating the crystallization and crystallization operation, the soluble solvent is preferably a mixture of diisopropyl ether and an alcohol, acetone, or ethyl acetate and is particularly preferably ethyl acetate.

To facilitate precipitation of the crystals, it is preferable to precipitate the crystals while the temperature of the mixture containing the compound 1 and the alcohol is controlled by, for example, cooling the mixture. The temperature of the mixture containing the compound 1 and the alcohol is −80° C. to +10° C., preferably −30° C. to 0° C., and more preferably −20° C. to −15° C.

A small amount of crystals can be obtained by cooling, to a very low temperature (e.g., −78° C.), a small amount of the compound 1 dissolved in a mixture of the soluble solvent and the alcohol. The obtained crystals may be added as seed crystals to the oily compound 1 or its solution to crystallize compound 1.

The amount of the solvent used, i.e., the soluble solvent, may be 0.1 to 20 times the amount of the compound 1 and is preferably 1 to 5 times. The amount of the alcohol mixed with the compound 1 is 1 to 20 times the amount of the compound 1 and preferably 5 to 15 times. When water is added to the mixture of the compound 1 and the alcohol, the amount of water used is 1 to 10 times the amount of the compound 1 and preferable 3 to 7 times. In the present specification, for example, the phrase "a solvent is used in an amount 10 times the amount of a compound" means that 10 mL of the solvent is used for 1 g of the compound.

By subjecting a suspension of the compound 1 obtained by crystallization thereof to filtration under room temperature conditions, wet crystals can be obtained. The wet crystals can be dried at a temperature of, for example, 40° C. or lower.

Properties of Crystals of Compound 1

The crystals of the compound 1 in this embodiment are a white to pale yellow crystalline powder. The melting point of the crystals of the compound 1 in this embodiment is 46° C. to 49° as measured using a hot plate method melting point meter with the crystals sandwiched between cover glasses. A powder X-ray diffraction image of the crystals of the compound 1 in this embodiment that is observed by a powder X-ray diffraction method using CuKα radiation with 2θ representing a diffraction angle contains the following peaks. 2θ: 9.7, 12.9, 16.4, 16.8, 17.6, 19.5, 21.7, 22.6, 22.9, 23.3, 24.5, 24.8, 26.0, 26.4, 27.2

Specifically, for example, with the crystals of the compound 1 in this embodiment, a powder X-ray diffraction image substantially the same as that shown in FIG. 1 is obtained by powder X-ray diffraction.

The powder X-ray diffraction can be performed by, for example, using an apparatus and operating conditions used in Test Example 2 described later.

In thermogravimetric/differential thermal analysis (TG/DTA) of the crystals of the compound 1 in this embodiment, no weight loss is found until 49° C., which is a temperature relating to melting, and a single endothermic peak is found at around 50° C. Specifically, for example, the crystals of the compound 1 in this embodiment show substantially the same thermogravimetric/differential thermal analysis (TG/DTA) pattern as that shown in FIG. 2.

The thermogravimetric/differential thermal analysis (TG/DTA) can be performed by, for example, using an apparatus and operating conditions used in Test Example 3 described later.

Suspension Purification of Crystals of Compound 1

The crystals of the compound 1 in this embodiment can be purified by suspending and stirring the crystals, for example, in a lipophilic solvent in which the crystals exhibit poor solubility. The "lipophilic solvent in which the crystals of the compound 1 exhibit poor solubility" means a lipophilic solvent that can be used for suspension stirring of the crystals of the compound 1 when the temperature of the solvent is equal to or lower than the melting point of the compound 1.

Examples of the lipophilic solvent in which the crystals of the compound 1 exhibit poor solubility may include: aliphatic hydrocarbon solvents such as hexane, cyclohexane, and heptane; ether solvents such as diisopropyl ether and methyl-t-butyl ether; and mixtures thereof. The lipophilic solvent in which the crystals of the compound 1 exhibit poor solubility may contain the above-described soluble solvent so long as the resultant solvent has the property that the solubility of the crystals of the compound 1 in the resultant solvent is low.

From the viewpoint of purification efficiency, the lipophilic solvent in which the crystals of the compound 1 exhibit poor solubility is preferably a solvent that can be used for suspension stirring of the crystals of the compound 1 when the temperature of the solvent is 20° C. to 40° C. and more preferably a solvent that can be used for suspension stirring of the crystals of the compound 1 when the temperature of the solvent is 25° C. to 35° C. Still more preferably, diisopropyl ether or a mixture of hexane and diisopropyl ether may be used as the lipophilic solvent in which the crystals of compound 1 exhibit poor solubility. The mixing ratio of hexane to diisopropyl ether may be 0 to 10 parts by volume of hexane to 1 part by volume of diisopropyl ether and preferably 1 part by volume of hexane to 1 part by volume of diisopropyl ether.

The stirring temperature may be a temperature at which the crystals do not melt and is preferably 20° C. to 40° C. and more preferably 25° C. to 35° C. The length of stirring time is not particularly limited. However, from the viewpoint of improving the purity of the crystals, the stirring time is, for example, 1 hour to 100 hours and preferably 20 hours to 40 hours.

In Patent Literature 2, the compound 1 was obtained as a high-viscosity oily product. The crystals of the compound 1 in this embodiment can be more easily stored and transported as compared to the conventionally known high-viscosity oily compound and have excellent storage stability. In addition, purification of the crystals is easy. The crystals of the compound 1 in this embodiment, for example, can be used as an advantageous intermediate for producing 2-amino-2-[2-[4-(3-benzyloxyphenylthio)-2-chlorophenyl]ethyl]-1,3-propanediol hydrochloride.

EXAMPLES

The present invention will next be described more specifically by way of Examples. However, the present invention is not limited to the following Examples.

Example 1

Crystallization of Compound 1 (1)

A 3 L four-necked flask was charged with the oily compound 1 (115 g) and 230 mL of ethyl acetate to dissolve the compound 1. 115 mL of methanol was added to the obtained solution of the compound 1. After it was confirmed that the compound 1 was dissolved, the solution was cooled. Crystallization was found to occur at −18.9° C., and stirring was performed for 15 minutes. 1,035 mL of methanol was added dropwise to the suspension at −19.6 to −16.6° C., and then 575 mL of water was added dropwise at −18.1 to −2.7° C. The suspension was cooled to −20.0° C., and precipitated crystals were filtered using a 9.5 cm Kiriyama-funnel (paper filter No. 3). The precipitated crystals were washed with a mixed solvent of 518 mL of methanol and 57.5 mL of water and then deliquored for 30 minutes to obtain 118 g wet crystals. The wet crystals were dried using an air blow dryer set at 35° C. for 19 hours to obtain 110 g crystals of the compound 1 as a white powder (recovery: 95.8%).

Melting point: 47.3 to 47.8° C. (hot plate method)
Elemental Analysis: Calcd. $C_{22}H_{20}ClNO_3S$: C, 63.84; H, 4.87; N, 3.38.
Measured: C, 63.78; H, 4.85; N, 3.24.
EI-MS: m/z 413 (M$^+$).
1H-NMR (CDCl$_3$, 500 MHz) δ: 2.32 (2H, quin, J=6.9 Hz), 2.81 (2H, t, J=7.6 Hz), 4.40 (2H, t, J=6.9 Hz), 5.03 (2H, s), 6.90-6.98 (3H, m), 7.11-7.41 (9H, m).
FT-IR (ATR): 2937, 1586, 1548, 1473 cm$^{-1}$.

Example 2

Crystallization of Compound 1 (2)

Step of Preparing Solution of Compound 1

A 50 mL Erlenmeyer flask was charged with the compound 1 (7.00 g) and 7.0 mL of ethyl acetate, and the mixture was heated in a water bath at 35° C. to dissolve the compound 1. The obtained solution was filtered under reduced pressure using a glass filter, and the filtrate was collected in a 200 ml three-necked flask. The 50 mL Erlenmeyer flask was washed with 7.0 mL of ethyl acetate, and then 7.0 mL of methanol was added to the filtrate.

Step of Producing Seed Crystals 0.10 ml of the solution (the solution of the compound 1 in ethyl acetate (in an amount 2 times the amount of the compound 1) and methanol (in an amount equal to the amount of the compound 1)) was sampled. 0.20 mL of methanol was added to the sampled solution, and the resultant solution thereby yielded a white turbidity. The turbid solution was cooled in a coolant bath at −76° C. to crystallize the compound 1. The obtained crystals were used as seed crystals for the following recrystallization.

Recrystallization Step

The solution of the compound 1 obtained in the above step (the step of preparing the solution of the compound 1) was cooled and stirred, and the seed crystals obtained in the above step (the step of producing seed crystals) were added at −18.5° C. After the occurrence of crystallization was confirmed, the solution was stirred for 10 minutes. 63.0 mL of methanol was slowly added dropwise to the suspension at −19.8 to −15.2° C., and then 35.0 mL of purified water was slowly added dropwise at −19.9 to −14.3° C. The suspension was stirred at −20.2 to −16.2° C. for 10 minutes, and the precipitated crystals were filtered using a 6.5 cm φ glass filter. The precipitated crystals were washed with a mixed solvent of 31.5 mL of methanol and 3.5 mL of purified water. The washed crystals were deliquored for 1 hour to obtain 6.81 g of wet crystals. The wet crystals were dried under reduced pressure at room temperature for 3 hours and 20 minutes to obtain 6.81 g of crystals of the compound 1 as a white powder (recovery: 97.2%).

Melting point: 47.3 to 47.8° C. (hot plate method)

Example 3

Suspension Purification of Crystals of Compound 1

A 200 mL three-necked flask was charged with the crystals of the compound 1 (7.00 g) obtained in Example 1, 28.0 mL of hexane, and 28.0 mL of diisopropyl ether, and the mixture was stirred at 30.0 to 35.0° C. for 36 hours (9 hours/day, stirred for 4 days: the solution was left to stand at room temperature at night). During this process, part of the crystals were sampled from the suspension 1 to 3 days after the start of stirring, in order to check the degree of suspension purification.

After completion of the suspension purification, the suspension was stirred at 20.2 to 20.4° C. for 30 minutes, and the precipitated crystals were filtered using a glass filter (17G3.5). The precipitated crystals were washed with a mixed solvent of 31.5 mL of hexane and 10.5 mL of diisopropyl ether and then deliquored for 15 minutes to obtain 5.91 g of wet crystals. The wet crystals were dried under reduced pressure at room temperature for 4 hours and 10 minutes to obtain 5.90 g of crystals of the compound 1 as a white powder (recovery: 84.3%).

Melting point: 47.4 to 47.7° C. (hot plate method)

Example 4

Crystallization of Compound 1 (3)

A solution composed of the compound 1, solvent A and solvent B shown in TABLE 1 was cooled to a temperature shown as a crystallization temperature in TABLE 1 to precipitate crystals under cooling and stirring. Next, solvent C and solvent D shown in TABLE 1 were added to the suspension, and the resultant suspension was filtered at a temperature shown as a filtration temperature in TABLE 1 to filter out the crystals.

For example, Run 2 was performed according to the following procedure.

Procedure in Run 2: A mixture of the compound 1 (104 mg), IPE (0.50 mL), and methanol (0.10 mL) was heated to dissolve the compound 1 and then cooled to −20° C., and methanol (0.20 mL) was added. After the occurrence of crystallization was confirmed (−20° C.), the mixture was heated to 28° C. to dissolve most part of the crystals (part of the crystals remained undissolved). Methanol (0.70 mL) was added to the resultant mixture at 27° C., and then water (0.50 mL) was added at 27° C. After the mixture was cooled to 0° C., the crystals were collected by filtration and dried to obtain the compound 1 (90.4 mg) in a yield of 86.9%.

The same procedure was performed for Run 1 and Run 3 to 16. However, only in Run 16, seed crystals (weight not measured) were added together with the addition of methanol.

The results are shown in TABLE 1. In TABLE 1, IPE refers to diisopropyl ether, and IPA refers to 2-propanol.

TABLE 1

| Run | AMOUNT OF COMPOUND 1 USED | SOLVENT A (AMOUNT USED) | SOLVENT B (AMOUNT USED) | SOLVENT C (AMOUNT USED) | SOLVENT D (AMOUNT USED) | CRYSTALLIZATION TEMPERATURE[a] (FILTRATION TEMPERATURE) | RECOVERY | MELTING POINT (HOT-PLATE METHOD) |
|---|---|---|---|---|---|---|---|---|
| 1 | 103 mg | IPE (0.50 mL) | METHANOL (0.20 mL) | METHANOL (0.30 mL) | — | −20° C. (−18° C.) | 86.5% | 46~47° C. |
| 2 | 104 mg | IPE (0.50 mL) | METHANOL (0.30 mL) | METHANOL (0.70 mL) | WATER (0.50 mL) | −20° C. (0° C.) | 86.9% | 46~47° C. |
| 3 | 113 mg | IPE (0.50 mL) | ETHANOL (0.20 mL) | — | — | −15° C. (−15° C.) | 61.9% | 46~47° C. |
| 4 | 106 mg | IPE (0.50 mL) | ETHANOL (0.20 mL) | — | — | −10° C. (−10° C.) | 71.7% | 46~47° C. |
| 5 | 102 mg | IPE (0.50 mL) | ETHANOL (0.20 mL) | — | — | −21° C. (−21° C.) | 68.6% | 46~47° C. |
| 6 | 100 mg | IPE (0.50 mL) | ETHANOL (0.50 mL) | — | — | −20° C. (−20° C.) | 76.0% | 46~47° C. |
| 7 | 116 mg | IPE (0.23 mL) | ETHANOL (0.23 mL) | ETHANOL (0.46 mL) | — | −20° C. (−20° C.) | 77.6% | 46~47° C. |
| 8 | 107 mg | IPE (0.50 mL) | ETHANOL (0.15 mL) | ETHANOL (0.25 mL) | WATER (0.10 mL) | −20° C. (−20° C.) | 80.4% | 46~47° C. |
| 9 | 102 mg | IPE (0.40 mL) | ETHANOL (0.30 mL) | ETHANOL (0.50 mL) | WATER (0.40 mL) | −19° C. (−19° C.) | 81.4% | 46~47° C. |
| 10 | 112 mg | ETHYL ACETATE (0.20 mL) | METHANOL (0.10 mL) | METHANOL (0.90 mL) | — | −21° C. (−21° C.) | 83.9% | 47~48° C. |
| 11 | 102 mg | ETHYL ACETATE (0.20 mL) | METHANOL (0.40 mL) | METHANOL (0.60 mL) | WATER (0.50 mL) | −16° C. (0° C.) | 88.4% | 47° C. |
| 12 | 112 mg | ETHYL ACETATE (0.20 mL) | ETHANOL (0.20 mL) | ETHANOL (0.80 mL) | — | −20° C. (−20° C.) | 83.9% | 46~47° C. |
| 13 | 107 mg | ETHYL ACETATE (0.20 mL) | 1-PROPANOL (0.60 mL) | 1-PROPANOL (0.40 mL) | — | −21° C. (−21° C.) | 75.7% | 46~47° C. |
| 14 | 105 mg | ETHYL ACETATE (0.20 mL) | IPA (0.20 mL) | IPA (0.80 mL) | — | −20° C. (−20° C.) | 80.0% | 46~47° C. |
| 15 | 102 mg | ACETONE (0.20 mL) | METHANOL (0.10 mL) | METHANOL (0.90 mL) | — | −19° C. (−17° C.) | 82.5% | 46~47° C. |
| 16 | 102 mg | IPE (1 mL) | METHANOL (5 mL) | — | — | 0° C.[b] (−20° C.) | 69.9% | 46~47° C. |

[a]TEMPERATURE AT WHICH SOLUTION WAS COOLED TO START CRYSTALLIZATION
[b]TEMPERATURE AT WHICH SEED CRYSTALS WERE ADDED TO START CRYSTALLIZATION

Test Example 1

Effects of Suspension Purification of Compound 1 in Example 3 (HPLC Relative Purity)

During the suspension purification method in Example 3, a very small amount of the crystals were sampled from the suspension every one day (9 hours) of stirring and subjected to HPLC measurement. The results are shown in TABLE 3. A peak at a retention time of about 10.7 minutes is the peak of the compound 1.

Method of HPLC Measurement

10 µL of a 0.5 mg/mL solution prepared using the sampled crystals was tested by liquid chromatography under the following conditions.

Diluting solvent: Mixed solvent of acetonitrile for liquid chromatography/water (17:3)

Detector: Ultraviolet absorptiometer (measurement wavelength: 220 nm)

Column: A reversed phase column prepared by filling a stainless steel tube having an inner diameter of 4.6 mm and a length of 15 cm with octadecylsilanized silica gel of 5 µm for liquid chromatography (Inertsil ODS-3, manufacture by GL Sciences Inc.) was used.

Column temperature: Constant temperature around 30° C.

Mobile phase A: Diluted phosphoric acid (1→1,000)

Mobile phase B: Acetonitrile for liquid chromatography

Feeding of mobile phases: The mixing ratio of mobile phase A and mobile phase B was controlled as shown in TABLE 2.

Here, the diluted phosphoric acid (1→1,000) means that 1 mL of phosphoric acid was dissolved in water to make 1,000 mL.

TABLE 2

| TIME AFTER INJECTION (MINUTES) | MOBILE PHASE A (vol %) | MOBILE PHASE B (vol %) |
|---|---|---|
| 0~15 | 20 | 80 |
| 15~30 | 20→5 | 80→95 |
| 30~60 | 5 | 95 |

FLOW RATE: 1.0 mL PER MINUTE
AREA MEASUREMENT RANGE: 60 MINUTES

TABLE 3

| | RETENTION TIME (MINUTES) | AREA PERCENTAGE BEFORE SUSPENSION PURIFICATION (%) | AREA PERCENTAGE (%) IN SUSPENSION | | | |
|---|---|---|---|---|---|---|
| | | | ONE DAY AFTER (9 HOURS AFTER) | 2 DAYS AFTER (18 HOURS AFTER) | 3 DAYS AFTER (27 HOURS AFTER) | 4 DAYS AFTER (36 HOURS AFTER) |
| COMPOUND 1 | 10.629 | 97.55 | 98.39 | 98.49 | 98.56 | 98.59 |
| IMPURITY 1 | 11.662 | 0.90 | 0.57 | 0.55 | 0.54 | 0.52 |
| IMPURITY 2 | 23.617 | 0.49 | 0.30 | 0.29 | 0.29 | 0.28 |
| IMPURITY 3 | 41.862 | 0.35 | 0.30 | 0.28 | 0.28 | 0.27 |

As is clear from TABLE 3, main impurities during production of the compound 1, i.e., impurity 1 (retention time: about 11.7 (minutes)), impurity 2 (retention time: about 23.6 (minutes)), and impurity 3 (retention time: about 41.9 (minutes)), can be removed by simply suspending and stirring the crystals of the compound 1 in a solvent.

Test Example 2

Powder X-Ray Diffraction of Crystals of Compound 1

The crystals of the compound 1 obtained in Example 1 were filled into a filling portion of a glass-made flat plate sample holder and molded, and measurement was performed by a powder X-ray diffraction measurement method under the following operating conditions. The measurement results are shown in FIG. 1. The 2θ values (deg) of main peaks are shown in TABLE 4.

Apparatus Used

SmartLab (manufactured by Rigaku Corporation)

Operating Conditions

Tube current: 30 mA

Tube voltage: 40 kV

Scanning speed: 2° per minute

Divergence slit: 1°

Receiving slit: 0.15 mm

Scattering slit: 1°

Anticathode: Copper

Scanning range: 5 to 40°

Wavelength: CuKα/1.541867 angstroms

TABLE 4

| 2θ (deg) |
|---|
| 9.736 |
| 12.913 |
| 16.423 |
| 16.771 |
| 17.596 |
| 19.543 |
| 21.699 |
| 22.553 |
| 22.903 |
| 23.272 |
| 24.461 |
| 24.785 |
| 26.023 |
| 26.363 |
| 27.227 |

Test Example 3

Thermogravimetric/Differential Thermal Analysis (TG/DTA) of Crystals of Compound 1

Figure 2:
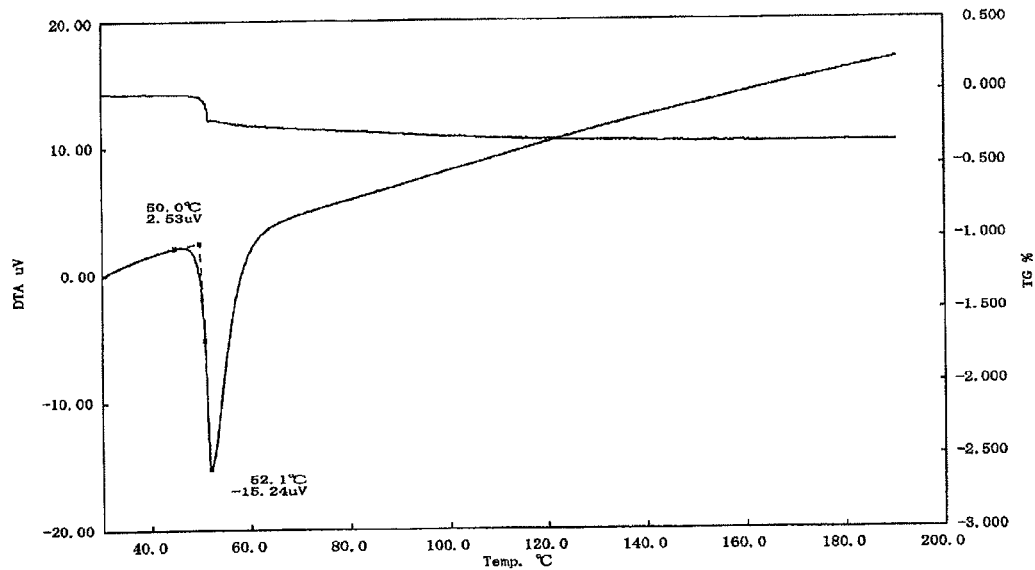
FIG. 2 is a diagram showing the results of thermogravimetric/differential thermal analysis (TG/DTA) of the crystal of 4-(3-benzyloxyphenylthio)-2-chloro-1-(3-nitropropyl)benzene in an Example.

The crystals of the compound 1 obtained in Example 1 were tested by a first thermal analysis method (differential thermal analysis: DTA) and a second method (thermogravimetric method: TG). The measurement results are shown in FIG. 2.

Apparatus Used

EXSTAR 6000 type, manufactured by Seiko Instruments Inc.

Operating Conditions

Amount of collected sample: 10 mg
Sample container: (Open) aluminum pan
Heating rate: 5° C. per minute
Measurement temperature range: 30 to 200° C.
Atmospheric gas: dry nitrogen
Flow rate of atmospheric gas: 100 mL per minute Test Example 4

Stability Test

The crystals of the compound 1 obtained in Example 1 were subjected to a stability test under accelerated conditions (40° C./75% RH) and long-term storage conditions (25° C./60% RH). No change in the appearance of the crystals was found 6 months after the start of the test under the accelerated conditions and also under the long-term storage conditions, and no decomposition products were formed.

As described above, although the crystals of the compound 1 according to the present embodiment have a very low melting point of 46 to 49° C., the crystals were stable not only under the long-term storage conditions but also under the accelerated conditions, and no changes in properties were found.

INDUSTRIAL APPLICABILITY

The compound 1 can be used as an intermediate for producing 2-amino-2-[2-[4-(3-benzyloxyphenylthio)-2-chlorophenyl]ethyl]-1,3-propanediol hydrochloride having excellent immunosuppressive action. Since the compound 1 can be collected in the form of crystals, the compound 1 is easy to handle and can be stored for a long time. In addition, impurities can be easily removed from the crystals in the present embodiment. From the above points of view, the present invention is industrially applicable.

The invention claimed is:

1. A crystal of 4-(3-benzyloxyphenylthio)-2-chloro-1-(3-nitropropyl)benzene, wherein, in powder X-ray diffraction using CuKα radiation with 2θ representing a diffraction angle, a powder X-ray diffraction image including the following 2θ peaks is observed: 2θ: 9.7, 12.9, 16.4, 16.8, 17.6, 19.5, 21.7, 22.6, 22.9, 23.3, 24.5, 24.8, 26.0, 26.4, 27.2.

2. The crystal of 4-(3-benzyloxyphenylthio)-2-chloro-1-(3-nitropropyl)benzene according to claim 1, wherein a melting point of the crystal measured by a hot plate method is 46° C. to 49° C.

3. The crystal of 4-(3-benzyloxyphenylthio)-2-chloro-1-(3-nitropropyl)benzene according to claim 1, wherein, in thermogravimetric/differential thermal analysis (TG/DTA) of the crystal, no reduction in weight is observed until 49° C., and a single endothermic peak is observed at around 50° C.

4. A production method of the crystal according to claim 1, the method comprising:
dissolving 4-(3-benzyloxyphenylthio)-2-chloro-1-(3-nitropropyl)benzene in a soluble solvent that can dissolve the compound to obtain a solution,
mixing the obtained solution of the 4-(3-benzyloxyphenylthio)-2-chloro-1-(3-nitropropyl)benzene with an alcohol to form a mixture of the 4-(3-benzyloxyphenylthio)-2-chloro-1-(3-nitropropyl)benzene and the alcohol,
wherein the soluble solvent is selected from the group consisting of ethyl acetate, ethyl acetate in combination with methanol, ethyl acetate in combination with ethanol, ethyl acetate in combination with 1-propanol, ethyl acetate in combination with 2-propanol, diisopropyl ether in combination with methanol, diisopropyl ether in combination with ethanol, and acetone in combination with methanol, and
wherein the alcohol is selected from the group consisting of methanol, ethanol, 1-propanol, and 2-propanol, and mixtures thereof.

5. The production method according to claim 4, further comprising adding water to the mixture containing the 4-(3-benzyloxyphenylthio)-2-chloro-1-(3-nitropropyl)benzene and the alcohol.

6. The production method according to claim 4, wherein the crystal is precipitated while a temperature of the mixture containing the 4-(3-benzyloxyphenylthio)-2-chloro-1-(3-nitropropyl)benzene and the alcohol is controlled within a range of −80° C. to +10° C.

7. A purification method of 4-(3-benzyloxyphenylthio)-2-chloro-1-(3-nitropropyl)benzene, the method comprising the step of suspending and stirring the crystal according to claim 1 in a lipophilic solvent in which the crystal exhibits poor solubility,
wherein the lipophilic solvent is a solvent mixture of hexane and diisopropyl ether.

8. A crystal of 4-(3-benzyloxyphenylthio)-2-chloro-1-(3-nitropropyl)benzene, wherein a powder X-ray diffraction image the same as an image in FIG. 1 is obtained by powder X-ray diffraction using CuKα radiation with 2θ representing a diffraction angle.

* * * * *